(12) United States Patent
Brouckaert et al.

(10) Patent No.: US 7,959,907 B2
(45) Date of Patent: Jun. 14, 2011

(54) METHOD OF TREATING CANCER BY COMBINATION THERAPY USING TNF AND ALPHA-GALACTOSYLCERAMIDE

(75) Inventors: Peter Brouckaert, Ghent (BE); Dirk Elewaut, Heusden (BE); Leander Huyghe, Aarsele (BE)

(73) Assignees: VIB VZW, Gent (BE); Universiteit Gent, Gent (BE)

( * ) Notice: Subject to any disclaimer, the term of this patent is extended or adjusted under 35 U.S.C. 154(b) by 0 days.

(21) Appl. No.: 12/449,652

(22) PCT Filed: Feb. 20, 2008

(86) PCT No.: PCT/EP2008/052055
§ 371 (c)(1),
(2), (4) Date: Dec. 17, 2009

(87) PCT Pub. No.: WO2008/101951
PCT Pub. Date: Aug. 28, 2008

(65) Prior Publication Data
US 2010/0166697 A1     Jul. 1, 2010

(30) Foreign Application Priority Data

Feb. 21, 2007  (EP) .................................. 07102787

(51) Int. Cl.
*A61K 45/00*   (2006.01)
*A61K 31/00*   (2006.01)
*A61K 38/00*   (2006.01)
*A01N 61/00*   (2006.01)

(52) U.S. Cl. .............................. 424/85.1; 514/1; 514/1.1
(58) Field of Classification Search ........................ None
See application file for complete search history.

(56) References Cited

U.S. PATENT DOCUMENTS

| 4,677,063 A | 6/1987 | Mark et al. |
| 4,677,064 A | 6/1987 | Mark et al. |
| 2004/0127429 A1 | 7/2004 | Tsuji |

FOREIGN PATENT DOCUMENTS

| EP | 609437 B1 | 7/1999 |
| WO | WO 97/12962 | 4/1997 |
| WO | WO 00/77168 A2 | 12/2000 |
| WO | WO 2005/003167 A1 | 1/2005 |
| WO | WO 2006/026389 | 3/2006 |
| WO | WO 2008/101951 A1 | 8/2008 |

OTHER PUBLICATIONS

Carswell EA, et al. Proc. Natl. Acad. Sci. 72(9):3666-3670, 1975.*
Giaccone G, et al. Clinical Cancer Research, vol. 8:3702-3709, 2002.*
Ten Hagen TLM, et al. Int. J. Cancer 87(6):829-837, 2000.*
Nakagawa R, et al. Cancer Research 58:1202-1207, Mar. 15, 1998.*
Mosteller RD. N. Engl. J. Med. Oct. 22, 1987;317(17):1098.*
PCT International Search Report, PCT/EP2008/052055, dated Jun. 30, 2008.
Inui et al., Neutralization of tumor necrosis factor abrogates hepatic failure induced by alpha-galactosylceramide without attenuating its antitumor effect in aged mice, Journal of Hepatology, 2005, pp. 670-678, vol. 43.
Metelitsa et al., Expression of CD1d by myelomonocytic leukemias provides a target for cytotoxic NKT cells, Leukemia, 2003, pp. 1068-1077, vol. 17.
Nakui et al., Potentiation of antitumor effect of NKT cell ligand, alpha-galactosylceramide by combination with IL-12 on lung metastasis of malignant melanoma cells, Clinical & Experimental Metastasis, 2000, pp. 147-153, vol. 18.
Nishi et al., Synergistic Effect of KRN7000 with Interleukin-15, -7, and -2 on the Expansion of Human Valpha24+Vbeta11+T Cells In Vitro. Human Immunology, 2000, pp. 357-365, vol. 61.
DeVita et al., Chapter 13, Biologic Therapy with TNF: Systemic Administration and Isolation-Perfusion, Biologic Therapy of Cancer, Second Edition, 1995, pp. 329-345.
Lejeune et al., Efficiency of recombinant human TNF in human cancer therapy, Cancer Immunity, Mar. 22, 2006, pp. 1-17, vol. 6, p. 6.
PCT International Search Report, PCT/EP2004/051327, dated Dec. 9, 2004.
PCT Written Opinion, PCT/EP2004/051327, dated Dec. 9, 2004.
Brown et al., "Regulation of TRAF2 Signaling by Self-Induced Degradation," The Journal of Biological Chemistry, May 31, 2002, pp. 19433-19438, vol. 277, No. 22.
Kavsak et al., "Samd7 Binds to Smurf2 to Form an E3 Ubiquitin Ligase that Targets the TGF-beta Receptor for Degradation," Molecular Cell, Dec. 2000, pp. 1365-1375, vol. 6.
Legler et al., "Recruitment of TNF Receptor 1 to Lipid Rafts Is Essential for TNF-alpha-Mediated NF-kappaB Activation," Immunity, May 2003, pp. 655-664, vol. 18.
Zapata et al., "TRAFI: Lord Without a RING," Science's STKE, May 21, 2002, pp. 1-5, vol. 2002, No. 133.
Fraker et al., Chapter 13, Biologic Therapy with TNF: Systemic Administration and Isolation-Perfusion, Biologic Therapy of Cancer, Second Edition, 1995, pp. 329-345.
Nakagawa et al., Treatment of Hepatic Metastasis of the Colon 26 adenocarcinoma with an α-Galactosylceramids, KRN7000, Cancer Research, Mar. 15, 1998, pp. 1202-07, vol. 58.

* cited by examiner

*Primary Examiner* — Robert Landsman
(74) *Attorney, Agent, or Firm* — TraskBritt, P.C.

(57) ABSTRACT

The invention relates to the treatment of cancer. More specifically the invention shows that the anti-cancer activity in mammals can be augmented by administering to the mammalian host a combination of a synergistically effective amount of TNF and alfa-galactosylceramide.

15 Claims, 2 Drawing Sheets

Fig. 1.A
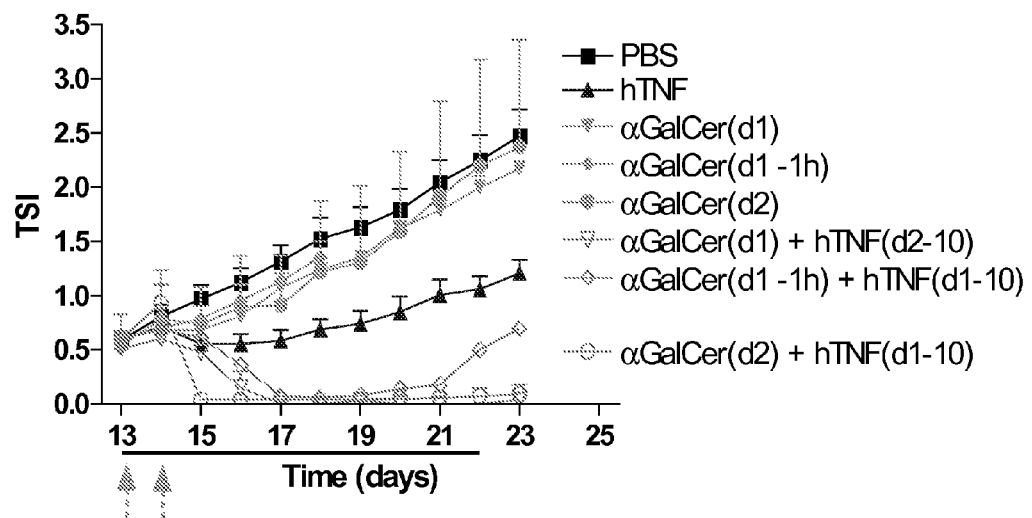
Fig. 1.B
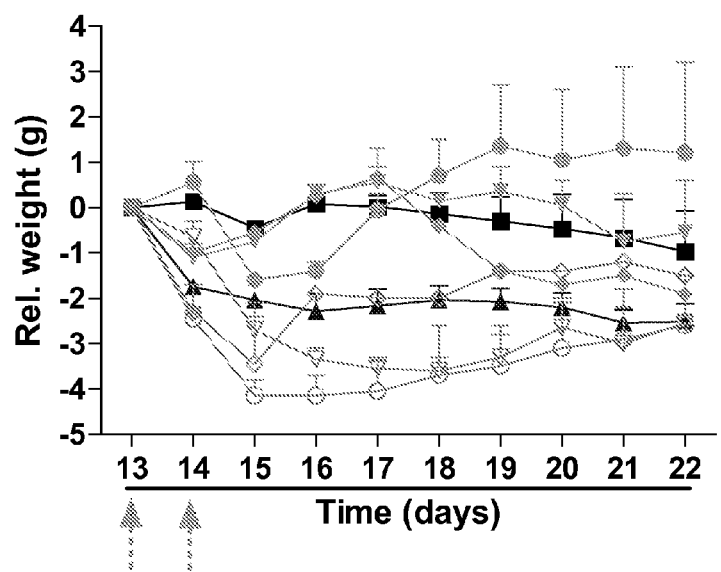

Fig. 2.A
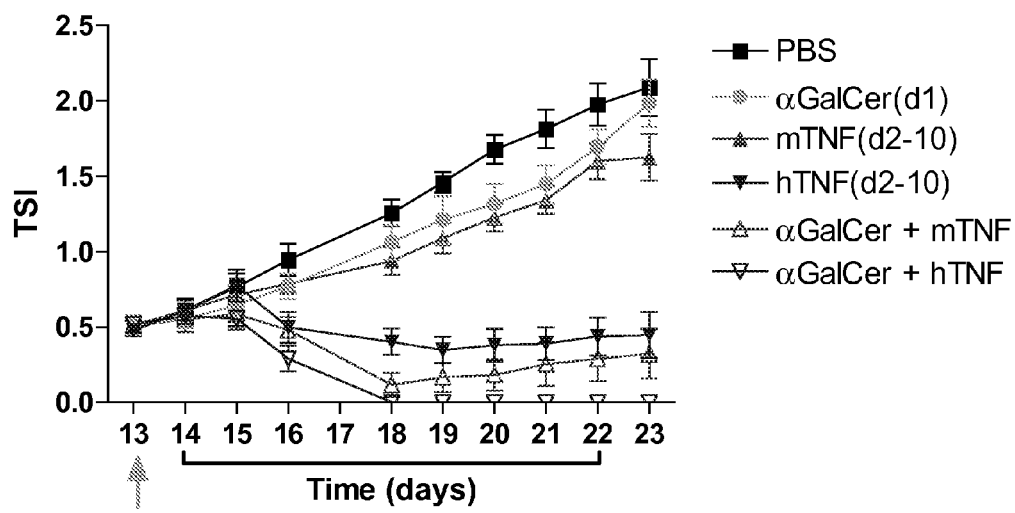
Fig. 2.B
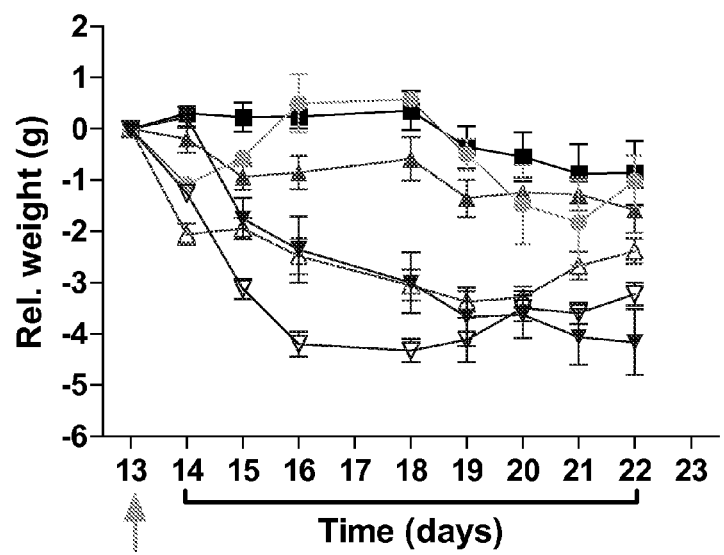

METHOD OF TREATING CANCER BY COMBINATION THERAPY USING TNF AND ALPHA-GALACTOSYLCERAMIDE

FIELD OF THE INVENTION

The invention relates to the treatment of cancer. More specifically the invention shows that the anti-cancer activity in mammals can be augmented by administering to the mammalian host a combination of a synergistically effective amount of TNF and alfa-galactosylceramide.

INTRODUCTION TO THE INVENTION

Combination therapy using two or more anti-cancer drugs to treat malignant tumours in humans is currently in use in research and in the clinic. The anti-cancer drugs may be anti-metabolites, alkylating agents, antibiotics, immune-stimulants, cytokines and the like. Combinations of said drugs are administered in an attempt to obtain a synergistic, cytotoxic effect on most cancers, e.g., carcinomas, melanomas, lymphomas and sarcomas, and to reduce or eliminate emergence of drug-resistant cells and to reduce side effects to each drug. Tumour Necrosis Factor (TNF), a protein of 157 amino acids, was originally discovered by Carswell et al (1975) (*Proc. Nat. Acad. Sci. USA,* 1975:72, 666) as a soluble factor released by the host after exposure to bacterial endotoxins and being responsible for tumour cytotoxicity. In addition to its antitumour effects, TNF is involved in immunoregulation, metabolism, haematopoiesis and musculoskeletal growth. However, TNF is very toxic and in attempts to evaluate TNF in the treatment of cancer, clinical trials have shown that hypotension, fever, chills, fatigue and headache were commonly observed precluding the systemic use of TNF. Alfa-galactosylceramides (alfa-GalCer) have originally been isolated from a marine sponge *Agelas mauritianus* and it was found that these compounds exhibit anti-tumour and immunostimulating activity in pre-clinical animal models (see for example patent EP0609437B1). KRN7000 is a synthetic alfa-GalCer that has been most frequently used in experimental studies. Clinical studies using KRN7000 have been disappointing since no clinical anti-tumour effects were recorded (Giaccone G et al (2002) *Clin Cancer Res* 8: 3702). Furthermore, recent studies point out that the use of sequential doses of alfa-GalCer can lead to an anergic state of T-cells (Parekh V V et al (2005) *J Clin. Invest.* 115(9):2572-83).

In the present invention we have found that the use of a sub-therapeutic amount of TNF in combination with an alfa-galactosylceramide provides a surprising synergism in treating various forms of cancer. In addition, we have shown that this synergistic combination does not have significant cytotoxic effects against normal cells and may thus be safely used to combat cancer.

FIGURES

FIG. 1.A-1.B Tumor experiment. The line under the graph represents the treatment period. The arrows indicate injection points of alpha-GalCer. Data are shown as mean±SEM. For PBS n=6, for human TNF (hTNF) n=7, for all other groups n=2. FIG. 1.A. Growth curves of subcutaneously growing B16B16 melanoma in C57BL/6 mice after treatment with alpha-GalCer (2 μg/mouse) and hTNF. FIG. 1.B. Relative body weight of the mice during treatment as a measure for systemic toxicity. Average body weight before treatment was 22.3 g (day 13). As used herein, "d1" means day 1, "d1-1h" means 1 hour before day 1, "d1-10" means days 1 to 10, and "d2-10" means days 2 to 10.

FIG. 2.A-2.B. Pre-treatment with alpha-GalCer sensitizes for sub-therapeutic TNF. The line under the graph represents the treatment period with hTNF or murine TNF (mTNF). The green arrow indicates the time of injection of alpha-GalCer. Data are shown as mean±SEM, n=7. FIG. 1.A. Growth curves of subcutaneously growing B16B16 melanoma in C57BL/6 mice after treatment with alpha-GalCer (1 μg/mouse), hTNF and low dose mTNF. FIG. 1.B. Relative body weight of the mice during treatment as a measure for systemic toxicity. Average body weight before treatment was 22.2 g (day 13).

AIMS AND DETAILED DESCRIPTION

The present invention relates to a combination of tumour necrosis factor (TNF) and alfa-galactosyl-ceramide and the use of said combination as an anti-tumour therapeutic agent. Accordingly, the present invention provides a pharmaceutical composition comprising TNF and alfa-galactosylceramide.

In a particular embodiment said pharmaceutical composition comprises synergistically effective amounts of TNF and alfa-galactosylceramide.

In another particular embodiment said TNF is from mammalian species, preferably human. In another particular embodiment said pharmaceutical composition is free of cells and free of lymphotoxin.

In yet another particular embodiment said TNF in said pharmaceutical composition is present in a sub-therapeutic amount. A sub-therapeutic effect of a compound (here TNF) means that no statistically relevant effect is observed on tumour growth when said compound is administered to a mammalian host carrying a tumour as a sub-therapeutic doses of said compound (i.e. here TNF) alone.

In yet another embodiment the pharmaceutical composition comprising TNF and alfa-galactosylceramide further comprises a chemotherapeutic agent.

In yet another embodiment the invention provides the use of a pharmaceutical composition comprising TNF and alfa-GalCer for the therapeutic treatment of cancer.

In yet another embodiment the use of a pharmaceutical composition comprising TNF and alfa-GalCer is used for the treatment of metastasis.

In a particular embodiment said TNF and alfa-galactosyl-ceramide are administered sequentially.

In another particular embodiment the administration of TNF precedes the administration of alfa-galactosylceramide.

In a preferred embodiment the administration of alfa-galactosylceramide precedes the administration of TNF.

In yet another preferred embodiment the administration of alfa-GalCer precedes the administration of TNF wherein said alfa-GalCer administration consists of a single dose which is administered at least one hour before the administration of TNF. In a particular embodiment said single dose of alfa-GalCer is administered at least 1, 2, 3, 4, 5, 6, 7, 8, 9, 10, 11 or 12 hours before the administration of TNF. In yet another particular embodiment said single dose of alfa-GalCer is administered at least one day before the administration of TNF. In yet another particular embodiment at least two doses of alfa-GalCer are administered before the administration of TNF.

Another preferred embodiment the administration with TNF is daily for at least 3, at least 4, at least 5, at least 6, at least 7, at least 8 or at least 9 consecutive days.

It should be clear to the skilled practitioner that the dose and dosage regimen will depend mainly on whether the TNF and an alfa-galactosylceramide are being administered separately or as a mixture, the type of cancer, the patient, and the patient's history. The amount must be effective to achieve a tumour reduction that is synergistic. If multiple doses are employed (such as preferred with TNF) the frequency of administration will depend, for example, on the type of host and type of cancer, dosage amounts, etc. For some types of cancers, daily administration will be effective, whereas for others, administration every other day or every third day will be effective, but daily administration will be ineffective. The practitioner will be able to ascertain upon routine experimentation which route of administration and frequency of administration are most effective in any particular case.

By "TNF" it is meant the various forms of TNF described below:

The cloning of human TNF having 151 and 155 amino acids (2 and 6 less than the native form) is disclosed in EP155,549 (Dainippon Pharmaceutical Co., Ltd.), and human TNF having 155 amino acids is disclosed in EP158, 286 (Asahi Kasei Kogyo Kabushiki Kaisha). The cloning of mature TNF (157 amino acids) and various modified forms (muteins) thereof is disclosed in EP168,214 (Genentech). The recombinant human TNF may be obtained as described by Pennica et al., Nature (1984), 312:724-729; Yamada et al., J. Biotechnology (1985), 3:141-153; Wang et al., Science (1985), 228:149-154, EP155,549 and EP168,214. The TNF is preferably human unglycosylated TNF having a molecular weight of about 15,000-20,000 daltons on SDS-PAGE. In a particular embodiment the TNF is a human TNF mutein wherein up to the first eight amino acid residues have been deleted, using the procedure described in U.S. Pat. No. 4,677,064 and U.S. Pat. No. 4,677,063 the TNF is a cysteine-depleted mutein described in U.S. Ser. No. 06/698,939. For human applications preferably the TNF is derived from human sources. Even more preferably, the TNF for human applications is recombinant unglycosylated human TNF. By "an alfa-galactosylceramide or alfa-GalCer" it is meant a derivative or an analogue derived from a glycosphingolipid that contains a galactose carbohydrate attached by an alfa-linkage to a ceramide lipid that has an acyl and sphingosine chains of variable lengths. KRN7000 (2S 3S, 4R)-1-O-(alfa-D-galactopyranosyl)-N-hexacosanoyl-2-amino-1,3,4-octadecanetriol) is a synthetic alfa-GalCer that has been most frequently used in experimental studies and also in example 1 of the present invention. The present invention also envisages alfa-galactosylceramides described in the patent EP0609437B1 (Kirin Beer Kabushiki Kaisha), in the application WO2006026389 (Albert Einstein College of Medicine of Yeshiva University), in the application US20040127429. In particular, in the latter application C-glycoside analogues of alfa-GalCer are described which are less susceptible to enzymatic degradation in vivo than the O-glycosides. A particular C-glycoside (an analogue of KRN7000) is described in Yang G. et al (2004) Angew. Chem. Int. Ed. 43, 3818-3822. The preferred range of alfa-GalCer used in the pharmaceutical composition of the present invention is between 20-200 µg/kg.

Thus the combination of alfa-galactosyl ceramide and TNF is found to provide a surprising synergism in treating various forms of cancer such as melanoma, lung carcinoma and lymphoma.

As used herein, the term "therapeutic" treatment refers to administration to the host of TNF and an alfa-galactosylceramide after the host has contracted cancer, as determined by any means. The treatment is not considered therapeutic if an existing tumour burden is not decreased or more preferentially eliminated.

As used herein, the term "cancer" refers to any neoplastic disorder, including such cellular disorders as, for example, renal cell cancer, Kaposi's sarcoma, chronic leukemia, breast cancer, sarcoma, ovarian carcinoma, rectal cancer, throat cancer, melanoma, colon cancer, bladder cancer, mastocytoma, lung cancer, mammary adenocarcinoma, pharyngeal squamous cell carcinoma, and gastrointestinal or stomach cancer. Preferably, the cancer is lung carcinoma, melanoma and lymphoma.

As used herein, the term "synergistically effective amount" as applied to TNF and an alfa-galactosylceramide refers to the amount of each component of the pharmaceutical composition which is effective for a decrease of tumour volume and which produces an effect which does not intersect, in a dose-response plot of the dose of TNF versus a dose of alfa-galactosylceramide versus decrease of tumour volume, either the dose TNF axis or the dose alfa-galactosylceramide axis. The dose response curve used to determine synergy in the art is fully described by Sande et al., p. 1080-1105 in A. Goodman et al, ed., the Pharmacological Basis of Therapeutics, MacMillan Publishing Co., Inc., New York (1980). The optimum synergistic amounts can be determined, using a 95% confidence limit, by varying factors such as dose level, schedule and response, and using a computer-generated model that generates isobolograms from the dose response curves for various combinations of the alfa-galactosylceramide and TNF. The highest decrease in tumour volume on the dose response curve correlates with the optimum dosage levels.

As used herein, the term "recombinant" refers to TNF produced by recombinant DNA techniques wherein generally the gene coding for the TNF is cloned by known recombinant DNA technology. The recombinant host may be eucaryotic or procaryotic host.

As used herein, the term "pharmaceutically acceptable" refers to a carrier medium that does not interfere with the effectiveness of the biological activity of the active ingredients and that is not toxic to the hosts to which it is administered.

The administration of the pharmaceutical composition of the invention may take place by any suitable technique, including parenteral administration. Examples of parenteral administration include subcutaneous, intravenous, intra-arterial, intramuscular, and intraperitoneal, with intraperitoneal administration(s) being preferred (for convenience) with murine models, and intravenous and subcutaneous being preferred for higher mammals.

The dosage amount which appears to be most effective herein is one which results in tumour regression or complete regression and is not toxic to the host. This optimum level will depend on many factors, for example, on the type of host and type of cancer, route, schedule of administration, existing tumour burden, the type of alfa-galactosyl ceramide and TNF, and the definition of toxicity. Toxicity to the host may be defined by the extent and type of side effects or by the amount of body weight loss or by death after a certain period of time. If body weight loss is the criterion for toxicity, typically a loss of 10-20% by weight will be tolerated, with greater than 20% loss being considered toxic.

If body weight loss of greater than 20% is considered toxic, if the host is murine, if the route of administration is intraperitoneal via a mixture prepared in vitro and is every day or every other day, the dosage level at each administration of recombinant produced subtherapeutic TNF is preferably about 20 to about 50 µg TNF per kg host weight (note that these sub-therapeutic levels are approximately 5-10 times less than the murine therapeutic levels). Calculated to human applications the TNF range is about 50 to about 300 µg/m².

For parenteral administration the pharmaceutical composition will generally be formulated in a unit dosage injectable form (solution, suspension, emulsion), preferably in a pharmaceutically acceptable carrier medium that is inherently non-toxic and non-therapeutic. Examples of such vehicles include saline, Ringer's solution, dextrose solution, mannitol and normal serum albumin. Non-aqueous vehicles such as fixed oils and ethyl oleate may also be used. The carrier medium may contain minor amounts of additives such as substances that enhance isotonicity and chemical stability, e.g., buffers and preservatives. TNF will typically be formulated in such carriers at a concentration of about 0.1 mg/ml to 20 mg/ml.

Alternatively, the pharmaceutical composition may be made into a sterile, stable lyophilized formulation in which the purified compounds (i.e. TNF and alfa-GalCer) can be admixed with a water-soluble carrier such as mannitol, which provides bulk, and a sufficient amount of a surfactant (such as for example sodium dodecyl sulfate) to ensure the solubility of the alfa-galactosyl ceramide in water. The formulation is suitable for reconstitution in aqueous injections for parenteral administration and it is stable and well-tolerated in human patients.

It should be clear that the pharmaceutical composition and its uses can also be applied for the treatment of veterinary animals. For such applications TNF may be prepared from tissue cultures or by recombinant techniques, and from any mammalian source, such as, e.g. rabbit, primate, pig, cow, cat and dog.

The various aspects of the invention are further described by the following examples, which are not intended to limit the invention in any manner.

Materials and Methods

1. Reagents

Recombinant human TNF (hTNF) and murine TNF (mTNF), produced by *Escherichia coli* containing an appropriate expression plasmid (Marmenout A. (1985) Eur J. Biochem. 152(3):515-22), were purified to apparent homogeneity. Specific activities were $6.1 \times 10^7$ IU/mg and $1.28 \times 10^8$ IU/mg, respectively, as determined by an L929s cytotoxicity assay as described (Takahashi et al., 1995). Both for hTNF and mTNF, the endotoxin content was <10 U/mg as assayed by a *Limulus* amoebocyte lysate assay (Coatest; Chromogenix, Stockholm, Sweden). The alpha-Galactosyl Ceramide (alpha-GalCer) used has the same structure as KRN7000 and was synthesized by the group of Serge Van Calenbergh at the Laboratory for Medical Chemistry (Ghent University, Belgium).

2. Mice

Female C57BL/6J@RJ mice were purchased from Janvier (Le Genest-Saint-Isle, France). The animals were housed in 14-10 hours light/dark cycles in a temperature-controlled, air-conditioned room, and received food and water ad libitum. The mice were used for the tumour experiment at the age of 8-12 weeks.

3. Tumour Cells

The melanin-positive melanoma B16B16 cells (Hart et al., 1979) were cultured in RPMI 1640 (Invitrogen) supplemented with 10% FCS, 50 IU/ml penicillin G, 50 µg/ml streptomycin sulphate, 2 mM L-glutamine and 0.4 mM Na-pyruvate. For tumor inoculation cells were detached from the culture flask by a short EDTA treatment, washed three times in endotoxin-free sterile PBS (Sigma), and resuspended in PBS at $6 \times 10^6$ cells/ml.

4. Tumour Experiment

On day 0, the mice were inoculated with $6 \times 10^5$ cells subcutaneously in the back just in front of the hind limb. Treatment was started when the tumor size index (TSI), i.e., the product of the largest perpendicular diameters in cm, reached 0.5 (day 13). Treatment with hTNF (30 µg/injection) or low dose mTNF (0.7 µg/injection) was given daily for 9 or 10 consecutive days via paralesional injection (subcutaneous injection near the site of the tumor, but outside the nodule). Alpha-GalCer (1-2 µg/injection) was injected intraperitoneally. All agents were diluted in PBS to a final volume of 100 µl/injection. Control mice were injected with 100 µl PBS. TSI and body weight were measured every day prior to injection and every two or three days when treatment was finished.

EXAMPLES

1. Synergism Between Alfa-GalCer and TNF

To determine whether activation of NKT cells would sensitize for a sub-therapeutic treatment with TNF, C57BL/6 mice bearing a subcutaneously growing B16B16 tumor were treated with a combination of the specific NKT cell agonist alpha-GalCer and either hTNF or low dose mTNF. We first performed a pilot experiment to assess what would be the optimal time point to inject the alpha-GalCer in comparison to TNF. Alpha-GalCer was injected either 1 day before, 1 hour before, or 1 day after treatment with TNF was started. In PBS treated mice, the tumors grew linearly. Treatment with alpha-GalCer or hTNF alone had respectively no effect on tumor growth nor any tumoristatic effect. However, the response to the combination of alpha-GalCer and hTNF was striking, with tumor regression (more than 25% decrease in tumor size) in all treated animals (FIG. 1.A). Moreover, complete regression (no palpable tumor) of the B16B16 tumor was obtained in both treated mice when alpha-GalCer was injected 1 day before hTNF, and in one of the two treated mice when alpha-GalCer was injected 1 day after treatment with hTNF was started. The combination treatment with alpha-GalCer and hTNF caused a moderate increase in systemic toxicity compared to hTNF alone (FIG. 1.B). One of the two treated mice died when alpha-GalCer was injected 1 hour before hTNF. From these results we concluded that the optimal time point to inject alpha-GalCer was 1 day before treatment with TNF was started.

Next, we performed a larger scale experiment to determine whether pre-treatment with alfa-GalCer would cause a significant increase of the anti-tumour effect of TNF. Treatment with alfa-GalCer or low dose mTNF alone had a small inhibiting effect on tumour growth, while the effect of hTNF was tumouristatic. The combination of alfa-GalCer with hTNF or low dose mTNF was clearly synergistic: treatment caused tumour regression in all treated animals (FIG. 2.A), which was complete in five of the seven treated animals for alfa-GalCer plus hTNF (2 mice died during treatment; for hTNF alone also 2 mice died during treatment), and four of the seven treated animals for alfa-GalCer plus low dose mTNF (1 mouse died during treatment; for mTNF alone also 1 mouse died during treatment). The combination of alfa-GalCer plus hTNF or low dose mTNF, however, did only cause a moderate increase in systemic toxicity compared to hTNF or low dose mTNF alone (FIG. 2.B).

Taken together, we have shown that specific activation of NKT cells by a single injection of alfa-GalCer can induce a selective increase of the anti-tumour effect of TNF.

The invention claimed is:

1. A method of treating cancer selected from the group consisting of sarcoma, lung carcinoma, melanoma, and lymphoma in a subject determined to be suffering therefrom, the method comprising:

administering tumor necrosis factor ("TNF") at a dosage of about 50 to about 300 μg/m$^2$ and alpha-galactosylceramide at a dosage of between 20 and 200 μg/kg to the subject in an amount effective to reduce the subject's tumor burden or eliminate the tumor burden in the subject so as to treat the cancer.

2. The method according to claim 1 wherein a single alpha-galactosylceramide dose is administered to the subject at least one hour before administering TNF to the subject.

3. The method according to claim 2 wherein TNF is administered daily to the subject for at least five (5) consecutive days.

4. The method according to claim 1, wherein the TNF is recombinant and human.

5. The method according to claim 1, further comprising administering a chemotherapeutic agent to the subject.

6. The method according to claim 4, wherein a single alpha-galactosylceramide dose is administered to the subject at least one hour before administering TNF to the subject.

7. The method according to claim 6, wherein TNF is administered to the subject daily for at least five (5) consecutive days.

8. The method according to claim 5, wherein a single alpha-galactosylceramide dose is administered to the subject at least one hour before administering TNF to the subject.

9. The method according to claim 8, wherein TNF is administered to the subject daily for at least five (5) consecutive days.

10. A method of treating a tumor selected from the group consisting of sarcoma, lung carcinoma, melanoma, and lymphoma in a mammal of the type comprising utilizing alpha-galactosylceramide to treat the tumor, the improvement comprising:
    parenterally administering to the mammal, in addition to the alpha-galactosylceramide, from about 50 to about 300 μg/m$^2$ of recombinant human tumor necrosis factor ("hTNF"),
    wherein the administration of alpha-galactosylceramide and the administration of hTNF work synergistically with one another as to achieve a tumor reduction in the mammal.

11. The method according to claim 10, wherein the administration of hTNF to the mammal precedes the administration of alpha-galactosylceramide to the mammal.

12. The method according to claim 10, wherein administration of alpha-galactosylceramide to the mammal precedes administration of hTNF to the mammal by at least one (1) day.

13. The method according to claim 10, wherein administration of hTNF to the mammal proceeds for more than three (3) days.

14. The method according to claim 13, wherein administration of hTNF to the mammal proceeds for more than five (5) days.

15. The method according to claim 14, wherein administration of hTNF to the mammal proceeds for more than seven (7) days.

* * * * *